(12) United States Patent
Elbaum

(10) Patent No.: US 7,177,694 B2
(45) Date of Patent: Feb. 13, 2007

(54) METHOD AND APPARATUS FOR CONTROLLING REPETITIVE NERVOUS SYSTEM MALFUNCTION

(75) Inventor: Hector Daniel Elbaum, Templestowe (AU)

(73) Assignees: Development One Ltd (VG); Wondertap Pty Ltd (AU)

( * ) Notice: Subject to any disclaimer, the term of this patent is extended or adjusted under 35 U.S.C. 154(b) by 690 days.

(21) Appl. No.: 10/398,770

(22) PCT Filed: Oct. 9, 2001

(86) PCT No.: PCT/AU01/01262

§ 371 (c)(1),
(2), (4) Date: Apr. 10, 2003

(87) PCT Pub. No.: WO02/30510

PCT Pub. Date: Apr. 18, 2002

(65) Prior Publication Data

US 2004/0030363 A1 Feb. 12, 2004

(30) Foreign Application Priority Data

Oct. 10, 2000 (AU) .................................. PR0616

(51) Int. Cl.
*A61N 1/36* (2006.01)
(52) U.S. Cl. .......................................... 607/45; 607/48
(58) Field of Classification Search ................ 607/2, 607/48, 62, 115, 144–145, 148–149
See application file for complete search history.

(56) References Cited

U.S. PATENT DOCUMENTS

| 4,842,607 | A | | 6/1989 | Repperger et al. |
|---|---|---|---|---|
| 5,562,707 | A | | 10/1996 | Prochazka et al. |
| 5,899,922 | A | * | 5/1999 | Loos ............................. 607/2 |
| 6,161,044 | A | * | 12/2000 | Silverstone ................... 607/45 |
| 6,366,813 | B1 | * | 4/2002 | DiLorenzo .................... 607/45 |
| 6,704,603 | B1 | * | 3/2004 | Gesotti ......................... 607/62 |

FOREIGN PATENT DOCUMENTS

| WO | WO 97/39796 A1 | 10/1997 |
|---|---|---|
| WO | WO 01/10375 A2 | 2/2001 |

* cited by examiner

*Primary Examiner*—Carl Layno
(74) *Attorney, Agent, or Firm*—Banner & Witcoff, Ltd.

(57) ABSTRACT

An apparatus and method for controlling the symptoms of repetitive nervous system malfunction in a person such as the symptoms of Parkinson's disease and other ailments which create unwanted movement of a part of the person's body. The apparatus includes a support member to be worn on or in close proximity to a part of a patient's body effected by malfunction. The support member includes an actuator array for applying output signals to the part of the patient's body to cancel out pulse signals caused by the malfunction, to at least reduce unwanted movement of the part of patient's body. The actuator array preferably includes skin contact devices. In one embodiment the apparatus includes a detector for detecting pulses produced by the patient and which create the unwanted movement. Processing means may be used to produce an output signal which cancels those pulses. A method of treating the symptoms of repetitive nervous system malfunction is also provided.

34 Claims, 4 Drawing Sheets

METHOD AND APPARATUS FOR CONTROLLING REPETITIVE NERVOUS SYSTEM MALFUNCTION

CROSS REFERENCE TO RELATED APPLICATIONS

This is a U.S. National Phase Application under 35 U.S.C. §371 of International Application No. PCT/AU01/01262 filed Oct. 9, 2001, which was published Under PCT Article 21(2), which claims priority to Australian Application No. PR0616, filed Oct. 10, 2000, the entire contents of which are incorporated herein by reference.

FIELD OF THE INVENTION

This invention relates to an apparatus for controlling repetitive nervous system malfunction in a person such as the symptoms of Parkinson's disease and other ailments which create unwanted movement of part of a persons body.

BACKGROUND

Parkinson's disease is a neurological disease due to failure of cells in the brain which produce neuro transmitters. One of the symptoms of Parkinson's disease is resting tremor which usually manifests in a persons arm but which also can result in tremor of other parts of the body. The tremor is caused by failure of nerve impulses in the brain and unwanted nerve pulses which are created elsewhere in a person's body. Presently, there is no cure for Parkinson's disease and little if anything available for treating the tremor symptom of this disease.

Other conditions which produce unwanted tremor in a person's body including Huntington's Chorea. This condition produces an intention tremor which manifests itself when a person attempts to move, for example, his or her arm. Once again, nerve impulses create a unwanted movement in the form of a tremor of part of the person's body.

Parkinson's disease and Hungtington's Chorea are extremely serious conditions and research work is being undertaken into causes and possible cures or these conditions. However, quality of life of a person who suffers from these diseases could be greatly improved if it would possible to treat the tremor symptom of these conditions.

The object of the present invention is to provide method and apparatus which are intended to treat the symptom of tremor created by repetitive nervous system malfunction in a patient.

SUMMARY OF THE INVENTION

The invention, in a first aspect, may be said to reside in an apparatus for controlling repetitive nervous system malfunction including:

a support member to be worn on or in close proximity to a part of a patient's body affected by the malfunction;

at least one output member carried by the support member for applying an output signal to the part of the patient's body to cancel out pulse signals caused by the malfunction to at least reduce unwanted movement of the part of the patient's body caused by the malfunction.

Since the symptoms or ailments which cause tremor or other unwanted movement of parts of a patient's body are created by nerve pulses supplied by the brain into various muscles, by supplying a signal from the output member which cancels out those pulses, the unwanted movement is at least reduced and most preferably completely eliminated thereby preventing the tremor symptom of the disease or ailment affecting the patient.

In one embodiment of the invention the output member includes an actuator array carried by the support member. The actuator array may be comprised by a mechanical vibration device, device emitting ultrasound waves or a needle array emitting magnetic-electrical pulses. Most preferably the devices which make up the array are skin contact devices and may be in the form of plates or the like which are intended to make contact with the patient's skin. In other embodiments the devices may be invasive and be formed by needles which intend to penetrate the patient's skin. However, because of the invasive nature of this technique it is less preferred than devices which merely receive or transmit signals by contact with the patient's skin.

In one embodiment of the invention the apparatus includes:

a memory for storing data relating to a patient's symptoms which create unwanted movement of part of the patient's body;

processing means for outputting signals to the output member based on the data stored in the memory so that the output member is controlled in accordance with the data stored in the memory to produce output signals of a required nature to cancel out the pulses which create the unwanted movement of the part of the patient's body.

Preferably the processing means controls parameters of the output signal including any one or more of the following:

frequency;
phase;
amplitude; and
time duration.

This embodiment of the invention has particular application if the nature of the symptoms which create unwanted movement in the patient's body are repetitive and involve no substantial variation over time. In this embodiment it is therefore possible for the nature of the pulses which create the unwanted movement to be analysed and for the apparatus to output the counter-pulses to cancel those pulses.

In another embodiment of the invention which can also be used in the abovementioned environment, but which also has application in situations where the nature of the pulse signals created by the brain are not repetitive and are more random in nature, the apparatus further includes a detector for detecting pulses produced by the patient and which create the unwanted movement of a part of the patient's body, processing means for receiving signals indicative of those pulses and for controlling the output member to produce an output signal which cancels those pulses.

Thus, in this embodiment of the invention the pulses which are produced in the patient's body are detected by the apparatus and the apparatus processor signals indicative of those pulses can be analysed so that required counter-pulses can be produced and applied to the patient to cancel out the pulses which create the unwanted movement and thereby eliminate the unwanted movement.

In this embodiment of the invention the detector is preferably also carried by the support member.

The number of output members and detectors carried by the support member will depend on the particular application and the patient concerned. The number of output members may be extremely high if a number of different muscles in a part of patient's body such as an arm, are affected by the ailment or if a number of regions of a few muscles are affected. Alternatively, if only one muscle or one region of a muscle is affected then the number of output members can be as little as one.

In the second embodiment of the invention which includes the detector, preferably a detector is arranged in close proximity to each of the output members so that the processing means can determine which of the detectors detects a pulse creating unwanted movement and supply an appropriate counter-output signal to the output member adjacent that detector for supplying the output signal to the patient's body at a position coincident with where the pulse is detected which creates the unwanted movement.

Preferably the detector is any suitable transducer for detecting biological electric pulses.

Preferably the processing means is programmed with data enabling the processing means to distinguish between pulses which create unwanted movement of the part of a patient's body and pulses which create movement which is required by the patient. Typically, pulses which produce unwanted movement such as tremor are very short duration and relatively high frequency pulses compared to pulses which create required movement of muscles such as normal arm movement or the like, which are usually considerably longer in duration or frequency.

In one embodiment of the invention the output member may also function as the detector for detecting the pulses which create the unwanted movement. In this embodiment the output member may be in the form of a micro-machined needle array carried by the support member and which detects pulses created by the patient which cause the unwanted movement and, under control of the processing means, outputs the output signals to cancel out those pulses.

In one embodiment of the invention the output member which is carried by the support member is connected to the processing means by a communication link so that the processing means can be carried by the patient remote from the support member and output member. The processing means is most preferably located on a circuit board which can be carried on a patient's belt or in a patient's pocket or anywhere else which is convenient.

Preferably the communication link includes an electrical cable for the transmission of electrical signals between the output member and the processing means. However, in other embodiments wireless, or over-the-air transmission between the processing means and the output member is possible such as electromagnetic radiation transmission such as infra-red transmission.

In one embodiment of the invention the processing means includes a digital signal processor connected to a memory and a switch member for enabling the control of transmission of signals in the processing means from the digital signal processor to the output member.

Preferably the switch means includes at least one multiplexer.

Preferably the at least one multiplexer is coupled to the output member, the multiplexer being coupled to a filter and amplifier and then to a digital to analogue converter for converting digital signals supplied by the digital signal processor to analogue signals to cause the output member to produce the output signal.

In the embodiment in which the detector is utilised, the detector is preferably connected to a second multiplexer which in turn is connected to a filter and pre-amplifier and then to an analogue to digital converter for converting analogue signals to digital signals, the analogue to digital converter being connected to a phase-locked loop bit detection system for locking the phase of the detected pulses and for enabling the digital signal processor to produce the output signal having the required phase and frequency to cancel out the pulse which causes the unwanted movement.

In the embodiment of the invention which utilises an output member which acts both as an output member and a detector, the output member is connected to a multiplexer which in turn is connected to the digital signal processor and also to a duplex circuit, the duplex circuit being connected to a first circuit having a pre-amplifier, an analogue to digital converter and a phase-locked loop circuit which is connected to the digital signal processor and a second circuit including an amplifier and a digital to analogue converter connected to the digital signal processor so that the duplex can switch between the supply of signals from the output member to the digital signal processor via the first circuit and the supply of signals from the digital signal processor to the output member via the second circuit.

Preferably the memory is connected to the digital signal processor.

The invention may also be said to reside in a method of treating the symptoms of repetitive nervous system malfunction including the steps of:

locating an output member in proximity to a part of a patient's body affected by the malfunction; and causing the output member to produce an output signal to the part of the patient's body to cancel out pulse signals caused by the malfunction to at least reduce unwanted movement of the part of the patient's body.

The method may include the step of causing the output signal to be created from data stored in a memory and which is processed by a processor coupled to the output member.

In other embodiments the output signal may be created by detecting the pulse signal created by the patient's body which causes the unwanted movement, processing the detected signal to create a control signal which is supplied to the output member to cause the output member to output the output signal.

Preferably the creation of the output signal is performed by a digital signal processor which carries out an algorithm to create the output signal by estimation theory to produce an output having the required frequency, magnitude and phase to cancel out the pulse signal which causes the unwanted movement.

The invention may also be said to reside in a method of treating the symptoms of repetitive nervous system malfunction, including:

detecting pulses in a patient's body which create unwanted movement of a part of the patient's body;

analysing those pulses to enable the production of an output signal which can be applied to a patient's body to cancel out those pulses to prevent the unwanted movement.

Preferably this method includes detecting the pulses in the patients body, converting the signals to digital signals, determining the phase and magnitude of these signals, creating an output signal of opposite phase and same magnitude, and storing data relating to the output signal for supply to an apparatus to be worn by the patient for controlling the symptoms of the malfunction.

Preferably the signals are stored in memory in a computer and are downloaded from the computer to an apparatus to be worn by the patient so that when the apparatus is worn by the patient the apparatus is controlled in accordance with the data downloaded so that the apparatus produces the output signal to treat the symptoms of the malfunction.

The invention also resides in an apparatus which can be used by a medical practitioner to diagnose the nature of pulses produced by a patient which created unwanted movement of parts of the patient's body and to store data relating to those pulses so that the data can be provided to an apparatus for producing a counter-signal to cancel out those pulses to at least reduce the unwanted movement.

This aspect of the invention may be said to reside in an apparatus for detecting pulses which create unwanted movement in a patient's body and producing data for enabling counter-pulses to be produced which when applied to the patient cancel out the pulses to at least reduce the unwanted movement, said apparatus including:

a detector for detecting pulses in a patient's body which create unwanted movement of a part of the patient's body;

processing means for analysing those pulses to determine parameters of the pulses and for producing data to enable the production of output counter-pulses which when applied to a patient will cancel out the pulses which create the unwanted movement.

Preferably the processing means is connected to a personal computer in which the data can be stored so that the personal computer can be used to download the data to an apparatus to be worn by the patient for producing the counter-pulses to cancel out the pulses which create the unwanted movement.

Preferably the apparatus includes a multiplexer connected to the detector, a filter and pre-amplifier, an analogue to digital converter for converting analogue signals detected by the detector to digital signals, a phase-locked loop for providing information relating to magnitude and phase, a digital signal processor connected to the phase-locked loop circuit for producing data relating to the pulse signal which will cancel out the pulse signal causing the unwanted movement.

Preferably the digital signal processor is connected to a personal computer via an interface circuit.

A further aspect of the invention relates to a patient stimulation system for supplying an output signal to a patient to determine whether the output signal is properly cancelling out pulses causing unwanted movement of part of a patient's body and therefore treating the symptoms of repetitive nervous system malfunction suffered by the patient.

This aspect of the invention has application for use by medical practitioners so that once data is obtained relating to the nature of output pulses which are required to alleviate the symptoms suffered by a patient, those signals can be applied by the apparatus to a patient in a medical environment to determine the accuracy of the data for producing required output pulses which will cancel out the pulses creating unwanted movement, and if necessary allow modification to the data so that the output pulses which are created are most effective in reducing or eliminating the unwanted movement.

This aspect of the invention may be said to reside in an apparatus for supplying output pulses to a patient for treating unwanted movement of part of a patient's body to determine the effectiveness of the application of the pulses and allowing modification of the pulses if required, said apparatus including:

an output member for location on a patient's body to provide output signals to a part of the patient's body for cancelling out pulse signals causing unwanted movement of the part of the patient's body;

processing means for supplying signals to the output member to cause the output member to generate the output signal and supply the output signal to the patient's body;

memory means for storing data related to the output signal; and means for enabling alteration of the data so that the data can be altered to thereby change the output signals if required to enhance the cancellation of the pulse signals which create the unwanted movement and thereby treat the unwanted movement of the patient's body.

Preferably the processing means includes a multiplexer coupled to a digital signal processor, and also coupled to a filter and pre-amplifier which is connected to a digital to analogue converter for converting digital signals to analogue signals for application to the output member to create the output signal, a memory connected to the digital signal processor, and a connector for connection to a computer to enable data to be downloaded to the memory for creating the output signal and also for manipulation of that data to change the data and therefore the output signal.

A further aspect of the invention resides in an apparatus for applying treatment signals to a patient to control unwanted movement of part of the patient's body, said apparatus including:

a support member to be worn on the patient's body, the support member having a periphery which is held in close proximity to the part of the patient's body;

at least one output member and/or at least one detector carried by the support member so that the output member and/or detector are in close proximity to the patient's body;

connecting means for connecting the apparatus to a processing circuit for the processing, detection, supply or manipulation of data for the production of an output signal to be supplied to the patient's body to cancel out pulses which create unwanted movement of the patient's body.

Preferably the support member is in the form of an elasticized sleeve.

However, depending on the part of the patient's body to which the apparatus is to be supplied the support member may take on different configurations.

BRIEF DESCRIPTION OF THE DRAWINGS

Preferred embodiments of the invention will now be described, by way of example, with reference to the accompanying drawings in which.

DETAILED DESCRIPTION OF THE PREFERRED EMBODIMENTS

Figure 1:
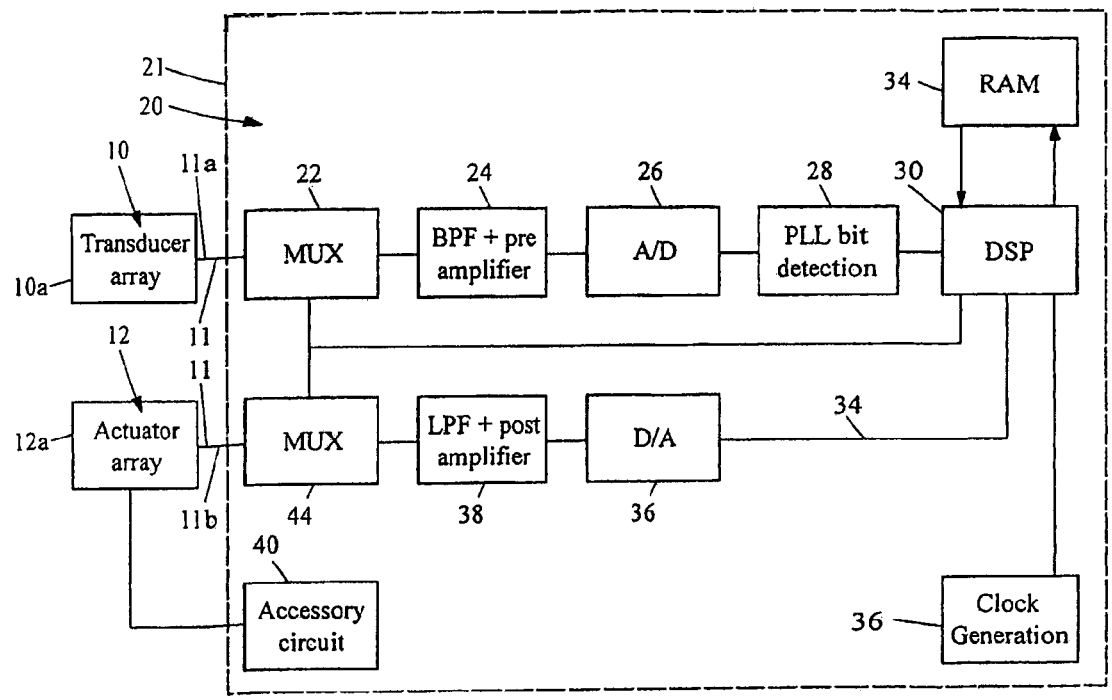
FIG. 1 is a schematic block diagram of a first embodiment of the invention.

With reference to FIG. 1, one embodiment of an apparatus for detecting and controlling the symptoms of repetitive nervous system malfunction is disclosed.

The embodiment of the invention includes detectors in the form of a transducer array 10 and an actuator array 12. The transducer array 10 and actuator array 12 are carried on a support member 50 (shown in FIG. 4) and which can be in the form of an elasticized sleeve, band or the like which is to be worn by a patient. The transducer array 10 and actuator array 12 are connected to a processing means 20 carried on a circuit board 21 shown in dotted lines in FIG. 1 by a communication link such as a cable 11. However, other forms of communication can be used such as electromagnetic radiation transmission for wireless communication such as infrared data transmission.

The circuit board 21 which carries the processing means 20 is carried by a patient by locating the board 21 on the patient's belt, in a pocket or anywhere else which is convenient.

The transducer array 10 is preferably any type of transducer which can detect electrical pulses generated in a patient's body and which will cause unwanted movement of a part of the patient's body. Suitable types of transducer include micro-machined needles, capacitor plates or other forms of electricity conductor which can detect and transmit electrical signals indicative of pulses which are generating in the patient's body to cause unwanted movement of part of the patient's body. The transducer array 10 will typically include a number of transducer elements which are supported on the support member in generally close proximity. The number of transducer elements in the array 10 will depend on the particular application of the invention and whether the nature of the treatment is localised on a patient and of a known nature or whether the treatment is to be less localised and is of a less known nature.

Figure 4:
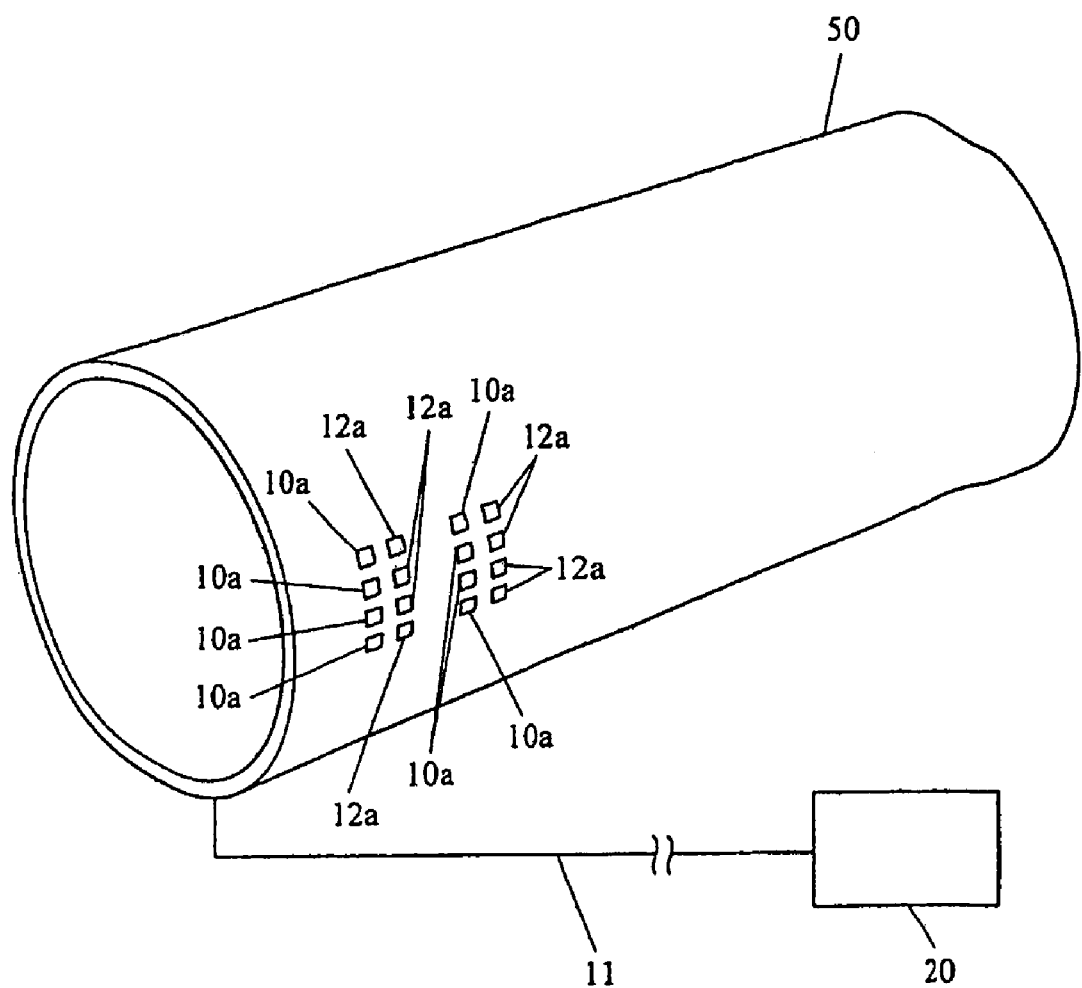
FIG. 4 is a drawing of one embodiment of the invention.

The transducer elements are shown on a support sleeve 50 in FIG. 4 and referenced by reference numeral 10*a*. It should be understood that the sleeve 50 can be completely covered with the transducers 10*a* and only a few are shown for ease of illustration in FIG. 4.

The actuator array 12 is any suitable array of elements which can supply required pulses to a patients body for cancelling out the unwanted pulses which are creating the unwanted movement. Such devices include mechanical vibration devices, ultrasound wave emitters and the aforesaid needle array which can emit magnetic-electrical waves or pulses to the patient's body.

In FIG. 1 line 11*a* of cable 11 connects to all of the transducer elements 10*a* in the array 10 so that the elements 10*a* are connected to a multiplexer 22. The multiplexer 22 is connected to a band pass filter and pre-amplifier 24 which in turn is connected to an analogue to digital converter 26 for converting analogue signals detected by the transducer array 10 into digital signals. The analogue to digital converter 26 is connected to a phase-locked loop circuit 28 which in turn is connected to a digital signal processor 30. The digital signal processor 30 is connected to a random access memory 34 and to a clock generation circuit 36 for generating clock signals for driving the digital processor 30. The multiplexer 22 is also connected to the digital processor 30 via a line 31.

The transducer array 10 detects various unwanted nerve signal pulses which create unwanted movement of the various parts of the patient's body, which may be caused by Parkinson's disease or other ailments, and signals output from the elements 10*a* are supplied by line 11*a* to the multiplexer 22. The multiplexer 22 determines which of the transducer elements 10*a* has detected the pulse so that the multiplexer 22 can act as a switching element to ensure correct transmission of data signals back and forward between the transducer array 10 (and the actuator array 12) and the processing means 20 on the circuit board 21. The signals are supplied from multiplexer 22 by the band pass filter and pre-amplifier 24 to the analogue to digital converter 26 and then to the phase-locked loop circuit 28 where phase and magnitude data relating to the signals is initially processed to produce data relating to the frequency of the signal and opposite phase of the signal. That data is supplied to the digital signal processor 30 to create an output control signal on line 35.

The digital signal processor 30 is under the control of software in random access memory 34 for operating the digital signal processor 30 and further processing the signals received from the phase-locked loop circuit 28 for creation of the control signals on line 35. The control signals on line 35 are supplied to a digital to analogue converter 36, which converts the signals to analogue form, which then pass through a low pass filter and amplifier 38 to a multiplexer 44 which is connected via line 11*b* to the actuator array 12.

The actuator array 12 may include elements 12*a* for the output of signals to be supplied to the body. As best shown in FIG. 4, the elements 12*a* are arranged with various ones of the elements 10*a* so that an element 10*a* and an element 12*a* are closely adjacent one and other. The multiplexers 22 and 44 are connected together via line 39 which in turn connects to line 31 so that the multiplexers 22 and 24 can ensure an appropriate output signal on line 35 which is in response to the detection of a signal from one of the elements 10*a* is supplied to an appropriate actuator element 12*a* adjacent that element 10*a* for application to the patient's body.

An accessory circuit 40 is connected to the actuator array 12 for assisting with the control of the actuator elements 12*a*. The accessory circuit 40 facilitates operation of the actuator array 12 and may perform such functions as power management and the like.

The digital signal processor 30 carries out the algorithms required for digital signal detection of the nerve pulses and processing such as AR, time-frequency and also produces the opposite phase pulse as determined by the phase-locked loop circuit 28. The digital signal processor 30 processes the data received by it by using estimation theory. The phase-locked loop circuit 28 receives information from each of the transducer elements 10*a* and locks the phase of each channel, relating to each one of the elements 10*a*, for transmission to the digital signal processor 30 which, from that information, creates the required output control signal to enable the output signal of opposite phase and same magnitude to be transmitted to the patient.

Thus, when the device of FIG. 1 is worn by a patient such as in a support sleeve 50 shown in FIG. 4, pulses which are creating unwanted movement of part of the patient's body (such as an arm) are detected and immediately counter-pulses are produced which are supplied to the patient's body by the actuator array 12 to cancel those pulses to stop the unwanted movement.

Although the embodiment of FIG. 1 includes the transducer array 11 for detecting the pulses, rather than detect the pulses, it is possible that data relating to the nature of the pulses produced by a patient can be acquired and if the nature of the pulses which create unwanted movement in the patient's body are consistent then the random access memory 34 can simply be programmed with data relating to those pulses so that the digital signal processor 30 merely generates counter-pulses to be supplied on line 11*b* to the actuator array 12 for the creation of output signals which will cancel those pulses without having to detect them via a transducer array 10. Thus, in this embodiment of the invention the transducer array 10, multiplexer 22, filter 24, analogue to digital converter 26 and phase-locked loop circuit 28 can be omitted because the nature of the pulses is already known and programmed into the random access memory 34. This embodiment therefore has particular application where the nature of pulses causing unwanted movement are easily determined and are constant.

The embodiment described with reference to FIG. 1 has application where the pulses may be more random in nature thereby requiring detection, analysis and the production of specific control signals to counter those pulses.

Figure 2:
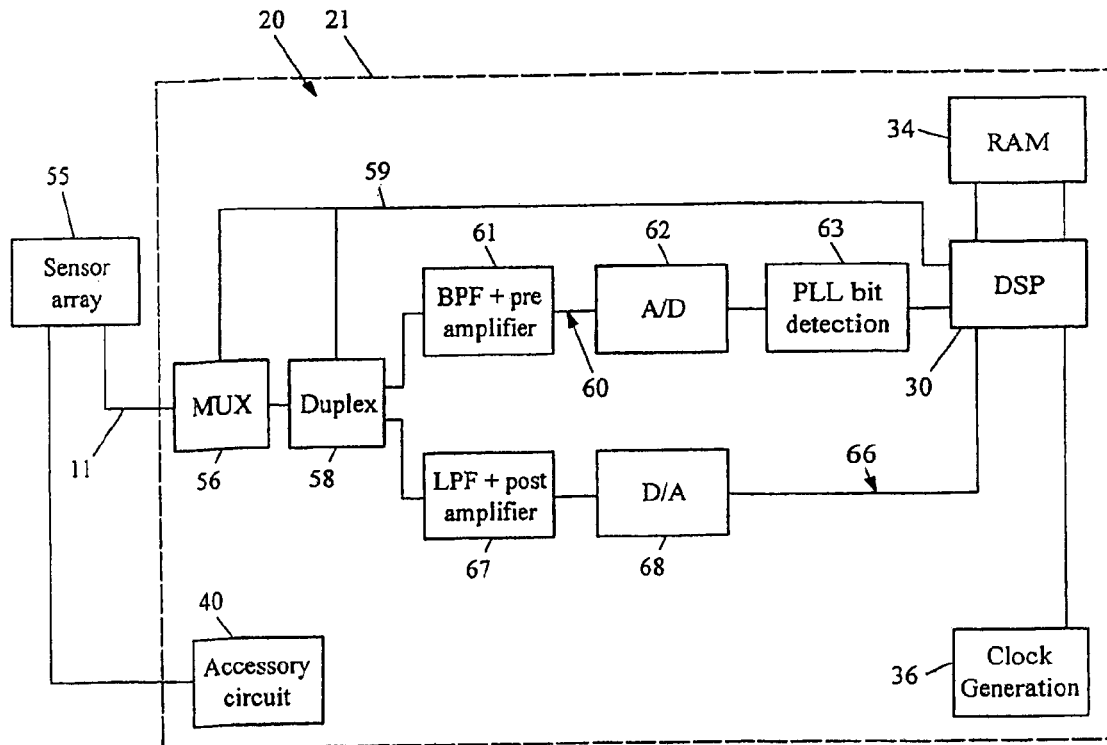
FIG. 2 is a schematic block diagram of a second embodiment of the invention.

FIG. 2 shows a further embodiment of the invention in which a sensor array 55 is used in place of the transducer array 10 and actuator array 12. The sensor array 55 performs the function of both detection of pulses and the application of output signals to the patient's body.

In this embodiment the sensor array 55 is connected to a multiplexer 56 which in turn is connected to a duplex circuit 58. The multiplexer 56 is connected to digital signal processor 30. The duplexer 58 also connects to the digital signal processor 30 as shown by line 59 in FIG. 2.

The duplex circuit 58 is connected via a first circuit branch 60 to the digital signal processor 30. The first circuit branch 60 includes a band pass filter and pre-amplifier 61, an analogue to digital converter 62 and a phase-locked loop circuit 63, each of which perform the same functions as the circuits 24, 26 and 28 described with reference to FIG. 1. The duplex circuit 58 is also connected to the digital signal processor 30 by a second circuit 66 which includes a low pass filter and amplifier 67 and a digital to analogue converter 68 so that output control signals generated by the signal processor 30 are supplied to the digital to analogue converter 68, for conversion to analogue form, and then to the duplex circuit 58, multiplexer 56 and to the sensor array 55 for causing treatment signals to be supplied to the patient's body to counter the pulses which are creating the unwanted movement. The multiplexer 56 and duplex circuits 58 switch between the branches 60 and 66 so that either the branch 60 is connecting the digital signal processor 30 to the sensor array 55 or the branch 66 is connecting the digital signal processor 30 to the sensor array 55. The multiplexer once again determines which of the various elements within the sensor array 55 is supplying signals for analysis and which is to receive signals for creating the output signal for application to the patient's body so that signals are supplied to the desired part of the patient's body to counter the unwanted pulses which are creating the unwanted movement.

Figure 3A:
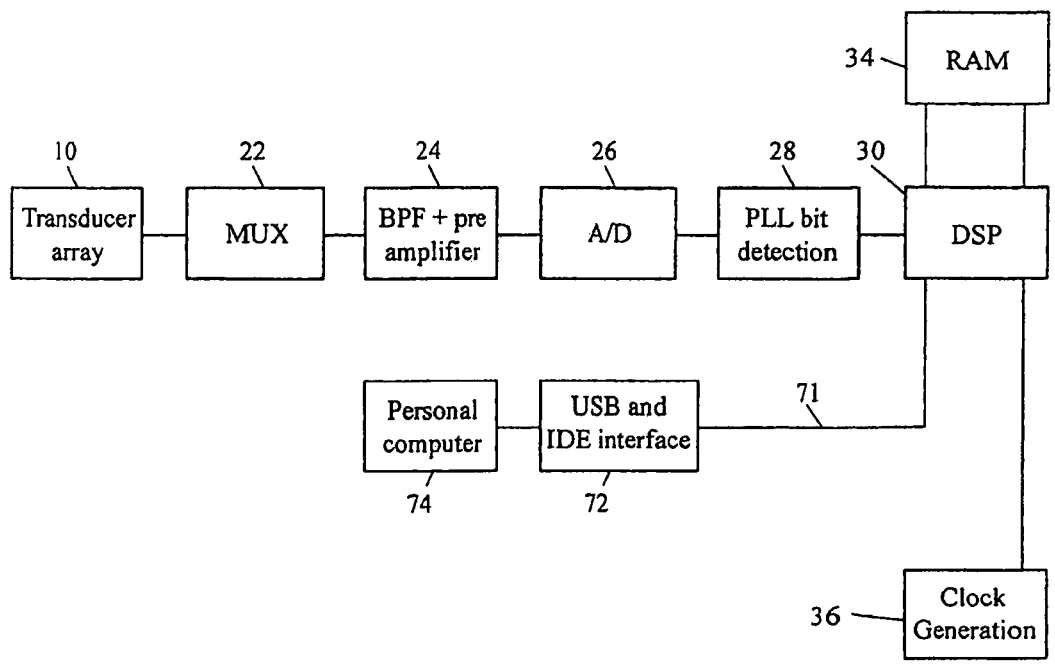
FIG. 3*a* is a schematic block diagram of a medical practitioner detection system according to one embodiment of the invention.
Figure 5A:
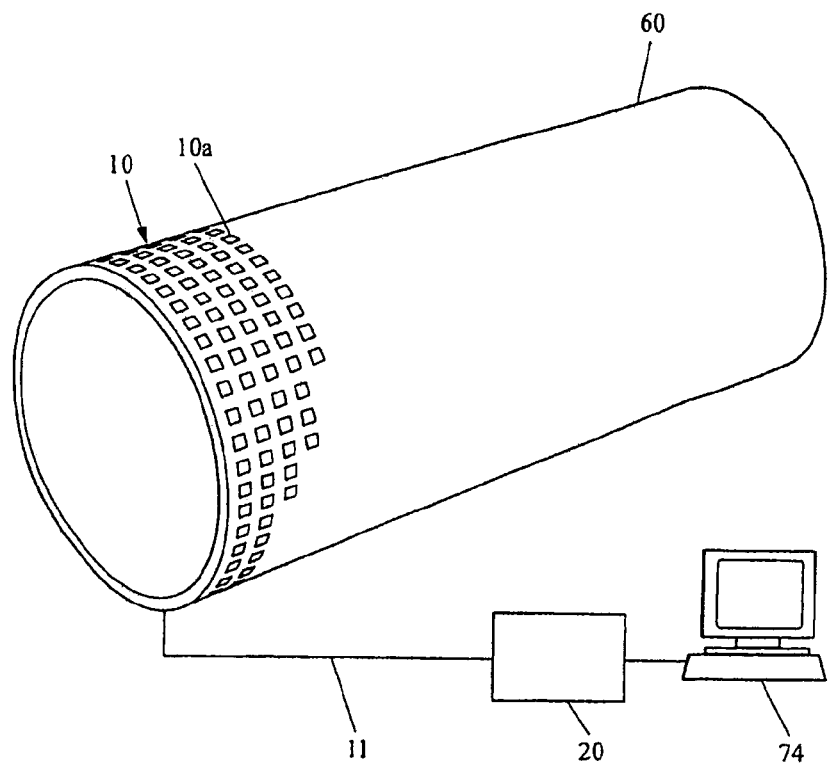
FIG. 5*a* is a drawing of another embodiment of the invention used for diagnostic purposes.

FIGS. 3a and 5a shows an embodiment of the invention which is for diagnostic use by a medical practitioner in order to provide data relating to the nature of pulses generating by a patient's body which are creating unwanted movement. FIG. 3a shows a schematic block diagram of the circuitry and FIG. 5a shows an embodiment of a diagnostic sleeve 60 to be worn by the patient. This embodiment has particular application in enabling the doctor to determine the nature of treatment signals which are required to treat the symptoms of the disorder to prevent the unwanted movement. The doctor is therefore able to download data to an apparatus of the type described with reference to FIG. 1 which does not have the transducer array 10 or the associated circuitry but just has an actuator array 12 for the application of output signals to the patient's body. Thus, by detecting, analysing and determining appropriate control signals by the device shown in FIG. 3a, data can be loaded into the memory 34 of FIG. 1 for the generation of appropriate control signals and output signals to be supplied by the actuator array 12 without the need for the device of FIG. 1 to detect the signals generated in the patient's body. As previously explained, this technique has great application in situations where the symptoms experienced by the patient are cause by constant and repetitive pulses.

With reference to FIG. 3a the apparatus has transducer array 10 which is the same as the transducer array 10 of FIG. 1. The transducer array 10 is connected to a multiplexer 22, a band pass filter and pre-amplifier 24 and analogue to digital converter 26 which, once again, are the same as those described with reference to FIG. 1. The analogue to digital converter is connected to a phase-locked loop circuit 28, also the same as that in FIG. 1, which in turn is connected to the digital signal processor 30, again the same as hat in FIG. 1. A random access memory 34 is provided for controlling operation of the digital signal processor 30 and a clock generator 36 supplies clocking signals to the processor 30 for controlling operation of the processor 30. The digital signal processor 30 is connected to an interface 72 which couples to a personal computer 74.

Figure 5B:
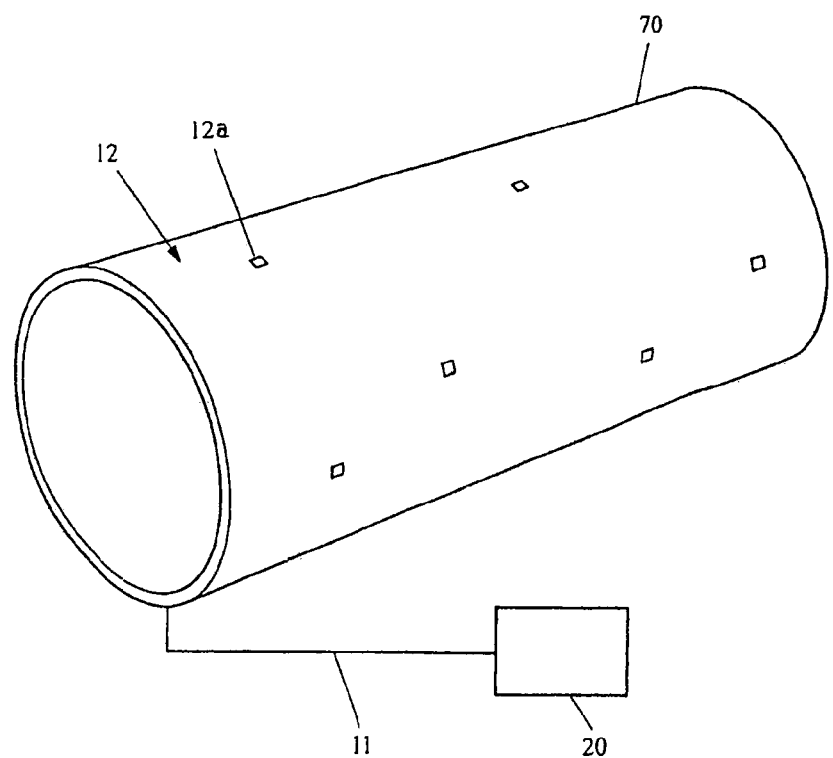
FIG. 5*b* is a drawing of a further embodiment of the invention used for treatment of a patient.

The transducer array 10 detects pulses in a human body in the manner described with reference to FIG. 1 and the digital signal processor 30 outputs a control signal on line 71 to the interface 72 after the data detected by the transducer array 10 has been processed in the same manner as described with reference to FIG. 1. Thus, a control signal 71 containing data relating to the nature of an output signal which should be applied to a patient to counter the pulses causing unwanted movement in the part of the patient's body is therefore generated. That data is fed to the personal computer 74 via the interface 72 and stored in the computer 74. The data which is stored in the computer 74 can be downloaded into the apparatus of FIG. 1 if the apparatus is to be used in the embodiment described without a transducer array 10 so that the digital signal processor 30 of FIG. 1 simply generates the required control signal on line 35 for the creation of the output signals by the actuator array 12. This embodiment enables the production of a specific apparatus for a particular patient which has actuator array elements 12a in the prescribed location for treating the symptoms experienced by that patient. One example is shown in FIG. 5b.

The device of FIG. 3a is used with a support member 60 (FIG. 5a), similar to that described with FIG. 4, in which the transducer elements 10a are provided completely over the entire surface of the support sleeve 60. The multiplexer 22 provides information as to which of the elements 10a is being energised by the pulses which are causing the unwanted movement so that the information provided to the computer 74 not only indicates the nature of the counter-signals which are required to cancel those pulses but also the locations from which they are generated.

This enables a custom made support member 70 (FIG. 5b) to be designed for the particular patient which has actuator array elements 12a only in the places where they are actually required, thereby reducing the cost of the support sleeve 70. Thus, the information which is stored in the computer 74 can be downloaded into a device of the type of FIG. 1 which omits the transducer array 10 and the associated circuitry so that the processor 30 and memory 34 are provided with information which is required in order to generate the required control signals on line 35 to enable the output signals to be generated by the actuator array 12. 10 In order to ensure that the elements 1 2a are located in the right part of the patient's body it is necessary to ensure the sleeve 50 or 70 is worn in the correct position and the information loaded into the personal computer 74 for downloading into the device of FIG. 1 may also include data relating to the required position at which the support sleeve 50 or 70 is intended to be worn.

Figure 3B:
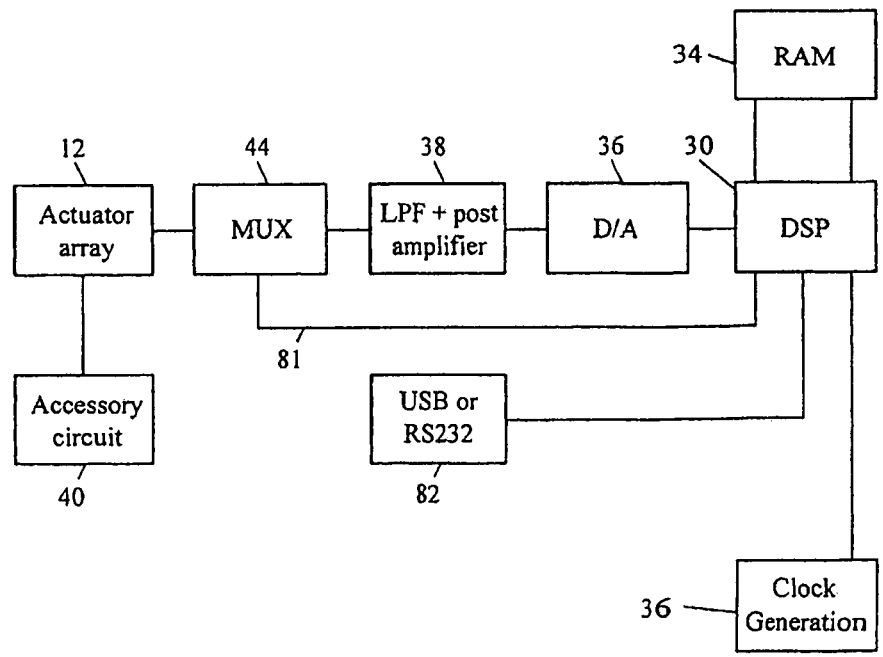
FIG. 3*b* is a schematic block diagram of a patient stimulation system used by a medical practitioner according to one embodiment of the invention.

FIG. 3b is a block diagram of a patient stimulation system which is intended to supply treatment signals to the patient for eliminating unwanted movement which enables the medical practitioner to alter the nature of the data which is to be stored if that is necessary.

The apparatus of FIG. 3b is intended to be used by a medical practitioner to test that data which is accumulated by the apparatus of FIG. 3a will correctly generate treatment signals for alleviating the symptoms of the patient. The actuator array 12 of FIG. 3b is the same as the actuator array 12 of FIG. 1, as is the multiplexer 44, low pass filter and amplifier 38 and digital to analogue converter 36 which connect to the digital signal processor 30. The random access memory 34 is again the same and includes information which controls operation of digital signal processor 30. Clock generator 36 is also provided for clocking the processor 30. The digital signal processor 30 also is connected to the multiplexer 44 via line 81 so the multiplexer can provide switching information relating to which of the elements in the actuator array 12 is providing data. The digital signal processor 30 is connected to a USB or RS232 connector 82 for connection a personal computer such as the personal computer 74 shown in FIG. 3a. In this embodiment the patient wears the support sleeve 50 which carries the actuator array 12 and the required signals are supplied to the digital signal processor 30 via the connector 82 from the personal computer 74. The digital signal processor 30 therefore provides signals via the digital to analogue converter 36, filter and amplifier 38 and multiplexer 44 to the actuator array 12 for the application of treatment signals to the patient. If the treatment signals are properly alleviating unwanted movement of the relevant part of the patient's body then the medical practitioner will know that the data which has been stored in the computer 74 is accurate and will properly function when loaded into a patient apparatus of the type described with reference FIG. 1 and/or FIG. 2. If the signals are not properly controlling unwanted movement then the medical practitioner can modify the data which is stored in the personal computer 74 so that modified data is supplied by the connector 82 to the digital signal processor 30 until the data correctly alleviates the unwanted movement of the patient's body. That modified data can then be supplied to the patient apparatus of FIGS. 1 or 2 for use by the patient.

Management and interface software for recording data from the patient and for controlling the downloading and manipulation of data is stored in the personal computer 74 used by the doctor.

Thus, according to the preferred embodiments of the invention, the patient can be provided with an apparatus which is specifically tailored to the patients needs with actuator output elements in a particular array within a support sleeve such as that shown in FIG. 5b, or other suitable support mechanism to be worn by the patient, for alleviating the patient's symptoms and in which the data is supplied by the medical practitioner using the equipment described with reference to FIGS. 3a or 3b. Alternatively the apparatus can be of the form which will generate its own control signals after detecting the pulses generated by the patient's body via a transducer array 10 as shown in FIG. 1 or a sensor array system as shown in FIG. 4.

FIG. 4 is a view showing one embodiment of the invention, intended to be worn on a patient's arm, in the form of a sleeve 50 formed from elastic type material. The sleeve 50 is completely covered over its length and periphery with actuator elements 12a and transducer elements 10a. Of course, if the device is intended for use with data supplied by the doctor, rather than data which is processed in the apparatus itself, then the transducer elements 10a are not required. The elastic nature of the sleeve 50 ensures that the elements 10a and 12a are closely adjacent a patient's skin for detecting and applying the appropriate pulse signals to the patient. Each of the elements 10a, 12a are connected to circuit board 21 via link 11 which may be a cable or over-the-air transmission system as previously described. The board 21 carries a processing means 20 and can be worn on a patient's belt or coat pocket or elsewhere as is required.

FIG. 5a is a view of another embodiment of a sleeve 60 intended for diagnostic use. The sleeve 60 includes a transducer array 10 made up of a plurality of transducer elements 10a covering the whole surface of the sleeve 60. The transducer array 10 is connected by a cable 11 to processing means 20 and computer 74.

FIG. 5b is a view of another embodiment of a sleeve 70 which has been made for a specific patient. The sleeve 70 includes an actuator array 12 made up of a plurality of actuator elements 12a arranged in a specific configuration as required to treat a specific patient. The actuator array 12 is connected by a cable 11 to processing means 20.

Although preferred embodiments of the invention are described herein in detail, it will be understood by those skilled in the art that variations may be made thereto without departing from the spirit of the invention or the scope of the appended claims.

The invention claimed is:

1. An apparatus for controlling repetitive nervous system malfunction including:
    a support member to be worn on or in close proximity to
        a part of a patient's body affected by the malfunction;
    at least one output member carried by the support member for applying an output signal to the part of the patient's body to cancel out pulse signals caused by the malfunction to at least reduce unwanted movement of the part of the patient's body caused by the malfunction;
    a detector for detecting pulses produced by the patient which create the unwanted movement of the part of the patient's body; and
    processing means for receiving signals indicative of those pulses and for controlling the output member to produce an output signal which cancels those pulses.

2. The apparatus of claim 1 wherein the output member includes an actuator array carried by the support member.

3. The apparatus of claim 1 wherein the actuator array includes a plurality of actuator elements, each actuator element being a skin contact device arranged to make contact with the patient's skin.

4. The apparatus of claim 1 wherein the detector is carried by the support member.

5. The apparatus of claim 1 wherein said detector is arranged in close proximity to each of the output members so that the processing means can determine which of the detectors detects a pulse creating unwanted movement and supply an appropriate counter-output signal to the output member adjacent that detector for supplying the output signal to the patient's body at a position coincident with where the pulse is detected which creates the unwanted movement.

6. The apparatus of claim 1 wherein the detector is any suitable transducer for detecting biological electric pulses.

7. The apparatus of claim 1 wherein the processing means is programmed with data enabling the processing means to distinguish between pulses which create unwanted movement of the part of the patient's body and pulses which create movement which is required by the patient.

8. The apparatus of claim 1 further including:
a memory for storing data relating to the patient's symptoms which create the unwanted movement of the part of the patient's body; and
processing means for outputting signals to the output member based on the data stored in the memory so that the output member is controlled in accordance with the data stored in the memory to produce output signals to cancel out the pulses which create the unwanted movement of the part of the patient's body.

9. The apparatus of claim 8 wherein the processing means controls parameters of the output signal including at least one of the following:
frequency;
phase;
amplitude; and
time duration.

10. The apparatus of claim 8 wherein the processing means includes a memory and a digital signal processor connected to a switch member for enabling the control of transmission of signals in the processing means from the digital signal processor to the output member.

11. The apparatus of claim 1 wherein the output member also functions as the detector for detecting the pulses which create the unwanted movement.

12. The apparatus of claim 11 wherein the output member is in the form of a micro-machined needle array carried by the support member and which detects pulses created by the patient which cause the unwanted movement and, under control of the processing means, outputs the output signals to cancel out those pulses.

13. The apparatus of claim 11 wherein the output member is connected to a multiplexer which in turn is connected to the digital signal processor and also to a duplex circuit, the duplex circuit being connected to a first circuit having a pre-amplifier, an analogue to digital converter and a phase-locked loop circuit which is connected to the digital signal processor and a second circuit including an amplifier and a digital to analogue converter connected to the digital signal processor so that the duplex circuit can switch between the supply of signals from the output member to the digital signal processor via the first circuit and the supply of signals from the digital signal processor to the output member via the second circuit.

14. The apparatus of claim 1 wherein the output member is connected to the processing means by a communication link so that the processing means can be carried by the patient remotely from the support member and output member.

15. The apparatus of claim 14 wherein the communication link includes an electrical cable for the transmission of electrical signals between the output member and the processing means.

16. The apparatus of claim 14 wherein the communication link is wireless, utilizing over-the-air transmission between the processing means and the output member.

17. The apparatus of claim 1 wherein the processing means includes a memory and a digital signal processor connected to a switch member for enabling the control of transmission of signals in the processing means from the digital signal processor to the output member.

18. The apparatus of claim 17 wherein the memory is connected to the digital signal processor.

19. The apparatus of claim 17 wherein the switch means includes at least one multiplexer.

20. The apparatus of claim 19 wherein the at least one multiplexer is coupled to the output member, the multiplexer being coupled to a filter and amplifier and then to a digital to analogue converter for converting digital signals supplied by the digital signal processor to analogue signals to cause the output member to produce the output signal.

21. The apparatus of claim 20 wherein the detector is connected to a second multiplexer which in turn is connected to a filter and pre-amplifier and then to an analogue to digital converter for converting analogue signals to digital signals, the analogue to digital converter being connected to a phase-locked loop bit detection system for locking the phase of the detected pulses and for enabling the digital signal processor to produce the output signal having the required phase and frequency to cancel out the pulse which causes the unwanted movement.

22. A method of treating the symptoms of repetitive nervous system malfunction including the steps of:
locating an output member in proximity to a part of a patient's body affected by the malfunction;
causing the output member to produce an output signal to cancel out pulse signals caused by the malfunction to at least reduce unwanted movement of the part of the patient's body;
detecting the pulse signal created by the patient's body which causes the unwanted movement; and
processing the detected signal to create a control signal which is supplied to the output member to cause the output member to output the output signal.

23. The method of claim 22 further including the step of causing the output signal to be created from data stored in a memory and which is processed by a processor coupled to the output member.

24. The method of claim 22 wherein creation of the output signal is performed by a digital signal processor which carries out an algorithm to create the output signal by estimation theory to produce an output having the required frequency, magnitude and phase to cancel out the pulse signal which causes the unwanted movement.

25. A method of treating the symptoms of repetitive nervous system malfunction, including:
detecting pulses in a patient's body which create unwanted movement of a part of the patient's body;
analyzing those pulses to enable the production of an output signal which can be applied to the patient's body to cancel out those pulses to prevent the unwanted movement.

26. The method of claim 25 further including the steps of:
converting the detected pulses to digital signals;
determining the phase and magnitude of the digital signals;
creating the output signal of opposite phase and same magnitude; and
storing data relating to the output signal for supply to an apparatus to be worn by the patient for controlling the symptoms of the malfunction.

27. The method of claim 25, further including the steps of:
storing the signals in memory in a computer; and
downloading the signals from the computer to an apparatus to be worn by the patient so that when the apparatus is worn by the patient the apparatus is controlled in accordance with the data downloaded so that the apparatus produces the output signal to treat the symptoms of the malfunction.

28. An apparatus for detecting pulses which create unwanted movement in a patient's body and producing data for enabling counter-pulses to be produced which, when applied to the patient, cancel out the pulses to at least reduce the unwanted movement, said apparatus including:

a detector for detecting pulses in a patient's body which create unwanted movement of a part of the patient's body;

processing means for analyzing those pulses to determine parameters of the pulses and for producing data to enable the production of an output signal containing counter-pulses which when applied to a patient will cancel out the pulses which create the unwanted movement.

29. The apparatus of claim 28 wherein the processing means is connected to a personal computer in which the data can be stored so that the personal computer can be used to download the data to an apparatus to be worn by the patient for producing the counter-pulses to cancel out the pulses which create the unwanted movement.

30. The apparatus of claim 28 further including a multiplexer connected to the detector, a filter and pre-amplifier, an analogue to digital converter for converting analogue signals detected by the detector to digital signals, a phase-locked loop for providing information relating to magnitude and phase, a digital signal processor connected to the phase-locked loop circuit for producing data relating to the pulse signal which will cancel out the pulse signal causing the unwanted movement.

31. An apparatus for supplying output pulses to a patient for treating unwanted movement of part of a patient's body to determine the effectiveness of the application of the pulses and allowing modification of the pulses if required, said apparatus including:

an output member for location on a patient's body to provide output signals to a part of the patient's body for canceling out pulse signals causing unwanted movement of the part of the patient's body;

a detector for detecting pulses produced by the patient which create the unwanted movement of the part of the patient's body;

processing means for supplying signals to the output member to cause the output member to generate the output signal and supply the output signal to the patient's body;

memory means for storing data related to the output signal; and means for enabling alteration of the data so that the data can be altered in response to the detected pulses to thereby change the output signals if required to enhance the cancellation of the pulse signals which create the unwanted movement and thereby treat the unwanted movement of the patient's body.

32. The apparatus of claim 31 wherein the processing means includes a multiplexer coupled to a digital signal processor, and also coupled to a filter and pre-amplifier which is connected to a digital to analogue converter for converting digital signals to analogue signals for application to the output member to create the output signal, a memory connected to the digital signal processor, and a connector for connection to a computer to enable data to be downloaded to the memory for creating the output signal and also for manipulation of that data to change the data and therefore the output signal.

33. An apparatus for applying treatment signals to a patient to control unwanted movement of part of the patient's body, said apparatus including:

a support member to be worn on the patient's body, the support member having a periphery which is held in close proximity to the part of the patient's body;

at least one output member and at least one detector for detecting pulses produced by the patient which create unwanted movement of the patient's body, the output member and detector being carried by the support member so that the output member and detector are in close proximity to the patient's body;

connecting means for connecting the apparatus to a processing circuit for the processing, detection, supply or manipulation of data for the production of an output signal to be supplied to the patient's body to cancel out pulses which create unwanted movement of the patient's body.

34. The apparatus of claim 33 wherein the support member is in the form of an elasticized sleeve.

* * * * *